(12) United States Patent
Cui et al.

(10) Patent No.: US 8,486,257 B2
(45) Date of Patent: Jul. 16, 2013

(54) BLOOD GLUCOSE SENSING

(75) Inventors: Yi Cui, Stanford, CA (US); Fabio La Mantia, Palermo (IT); Mauro Pasta, Ubiale Clanezzo (IT)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/136,970

(22) Filed: Aug. 16, 2011

(65) Prior Publication Data
US 2012/0043226 A1 Feb. 23, 2012

Related U.S. Application Data

(60) Provisional application No. 61/374,510, filed on Aug. 17, 2010.

(51) Int. Cl.
*G01N 27/327* (2006.01)

(52) U.S. Cl.
USPC .......................................................... 205/792

(58) Field of Classification Search
USPC ................ 204/403.01–403.07, 292; 205/787, 205/792
See application file for complete search history.

(56) References Cited

PUBLICATIONS

Tominaga, M., et al., "Surface poisoning during electrocatalytic monosaccharide oxidation reactions at gold electrodes in alkaline medium", Electrochemistry Communications, vol. 9, No. 8, Aug. 2007, p. 1892-1898.*
E.B. Makovos and C.C. Liu, "A cyclic-voltammetric study of glucose oxidation on a gold electrode", vol. 15, 1986, p. 157-165.*

* cited by examiner

*Primary Examiner* — J. Christopher Ball
(74) *Attorney, Agent, or Firm* — Lumen Patent Firm

(57) ABSTRACT

An oxidative peak in a cathodic scan is observed in the cyclic voltammetry of glucose at gold electrodes, its peak current density being proportional to glucose concentration in a wide potential range. The application of this phenomenon in blood glucose sensing has been hindered by the presence of inhibitors: the most problematic are chlorides due to their high concentration and difficult separation from glucose. The present invention provides a solution to this problem involving a three electrode, four step pulsed electrochemical detection technique.

2 Claims, 14 Drawing Sheets

Three Electrode Four Step Pulsed Technique

1$^{st}$ step: Chloride Removal

WE (Ag): $Ag + Cl^- \rightarrow AgCl(s) + e^-$

CE (Pt): $H_2O + 2e^- \rightarrow H_2 + 2OH^-$ pH from 7.4 to 11.5 (10% of Cl$^-$ removed)

2$^{nd}$ step: Gold Hydroxide Formation

WE (Au): $Au \rightarrow Au(OH)_3 + 3e^-$

CE (Pt): $H_2O + 2e^- \rightarrow H_2 + 2OH^-$

3$^{rd}$ step: Reduction of Gold Hydroxide and Glucose Sensing

WE (Au):

$Au(OH)_3 + 3e^- \rightarrow Au$

CE (Pt): $H_2O + 2e^- \rightarrow H_2 + 2OH^-$

4$^{th}$ step: Chloride Regeneration

WE (Ag): $AgCl(s) + e^- \rightarrow Ag + Cl^-$

CE (Pt): $2H_2O \rightarrow O_2 + 2H^+ + 2e^-$

Three Electrode Four Step Pulsed Technique

1st step: Chloride Removal

WE (Ag): Ag + Cl$^-$ → AgCl(s) + e$^-$

CE (Pt): H$_2$O + 2e$^-$ → H$_2$ + 2OH$^-$ pH from 7.4 to 11.5 (10% of Cl$^-$ removed)

2nd step: Gold Hydroxide Formation

WE (Au): Au → Au(OH)$_3$ + 3e$^-$

CE (Pt): H$_2$O + 2e$^-$ → H$_2$ + 2OH$^-$

3rd step: Reduction of Gold Hydroxide and Glucose Sensing

WE (Au):

Au(OH)$_3$ + 3e$^-$ → Au

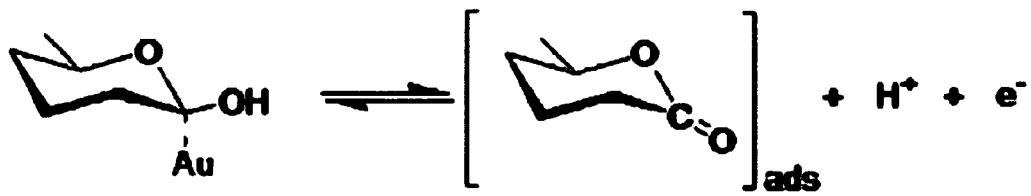

CE (Pt): H$_2$O + 2e$^-$ → H$_2$ + 2OH$^-$

4th step: Chloride Regeneration

WE (Ag): AgCl(s) + e$^-$ → Ag + Cl$^-$

BLOOD GLUCOSE SENSING

CROSS-REFERENCE TO RELATED APPLICATIONS

This application claims priority from U.S. Provisional Patent Application 61/374,510 filed Aug. 17, 2010, which is incorporated herein by reference.

FIELD OF THE INVENTION

The invention relates to blood glucose sensing methods and devices.

BACKGROUND OF THE INVENTION

Glucose sensors are of great interest for the medical application of blood glucose sensing. Their optimization (in terms of response time, lifetime, sensitivity and selectivity) is highly necessary to improve the treatment of Diabetes Mellitus, a chronic disease affecting millions of 37 people around the world.

Most studies on this subject have involved the use of enzymes. Although enzymatic detection usually shows good selectivity and high sensitivity, the enzyme is easily denatured during its immobilization process.

Non-enzymatic glucose sensors have been studied to develop an effective enzyme-free sensor; in particular the direct electrochemical oxidation of glucose in alkaline medium was investigated at Cu, Ni, Fe, Pt and Au electrodes. Of these electrodes, platinum was the most promising, but it proved to be extremely non-selective and susceptible to poisoning by various components of blood and other physiological media over extended use.

A different approach to the subject involves performing a cyclic-voltammetric study of glucose oxidation at a gold electrode. Using this approach, the occurrence of a positive current peak was observed during the cathodic sweep, and highlighted a highly linear dependence between current value maxima and glucose concentration. The application of the method in blood glucose sensing, however, has been hindered by the presence of inhibitors; chlorides, amino acids, and human albumin were observed to inhibit the reaction. Among them, chlorides are the most problematic because of their high concentration in the blood, (about 0.1 M) and the difficulty inherent in trying to separate them from glucose.

The present invention advances the art by providing new technology for blood glucose sensing to overcome at least some of these problems.

SUMMARY OF THE INVENTION

The present invention provides a method and device for electrochemically sensing glucose from a sample containing chlorides. A first working electrode (e.g. silver) is used for removing chlorides from the sample. A second working electrode (e.g. gold) is used for absorbing glucose from the sample. A current collector electrode (e.g. platinum) is used for establishing current flow between the first and second working electrodes, while during the removal of chlorides the pH of the sample increases towards basic pH. In one example, the pH increases to about 11.5 or at least 11.5. A sensing device is used for sensing oxidative current peaks caused by the absorption of the glucose. In general, the first and second working electrodes and the current collector electrode are made from non-toxic materials to the human body.

BRIEF DESCRIPTION OF THE DRAWINGS

FIG. 5 shows a four-step pulsed electrochemical detection schematic according to an exemplary embodiment of the invention.

Figure 11:
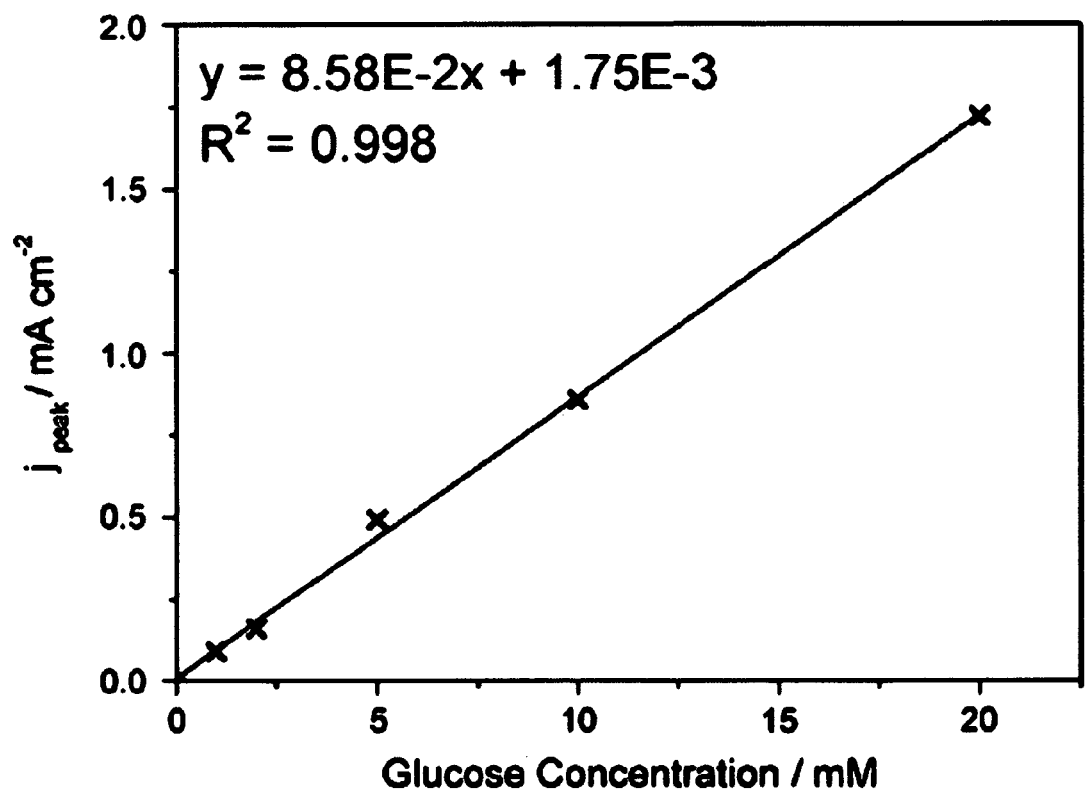
Figure 12:
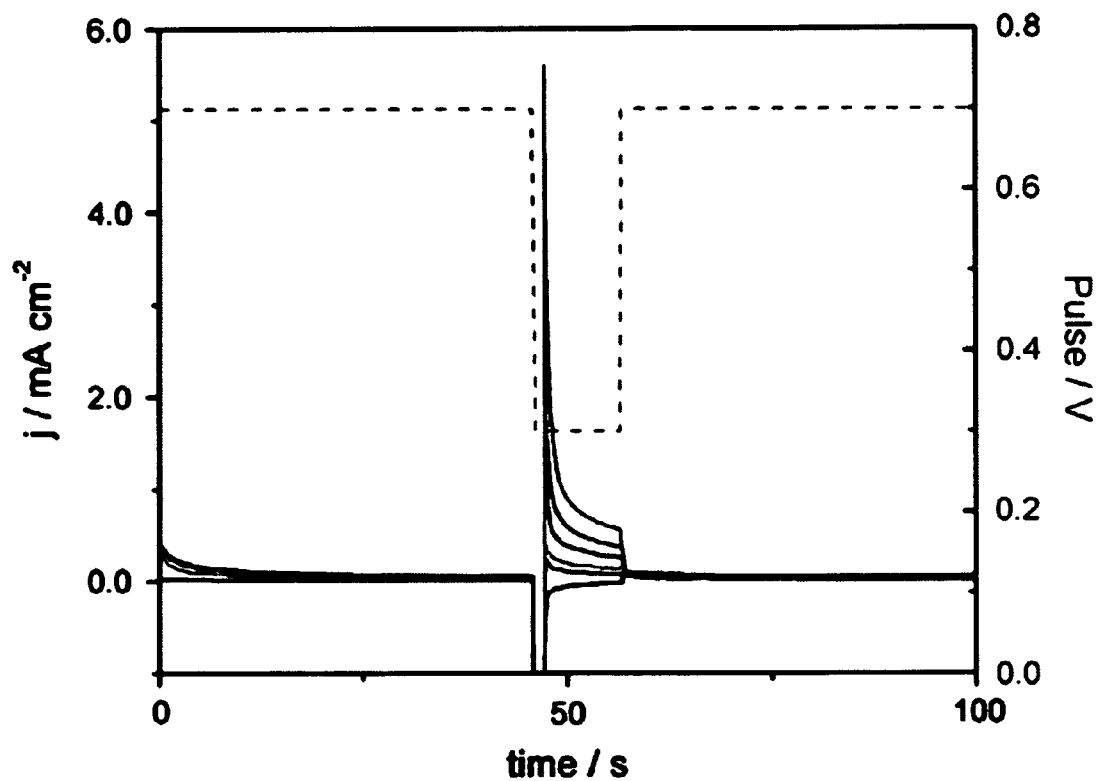
Figure 13:
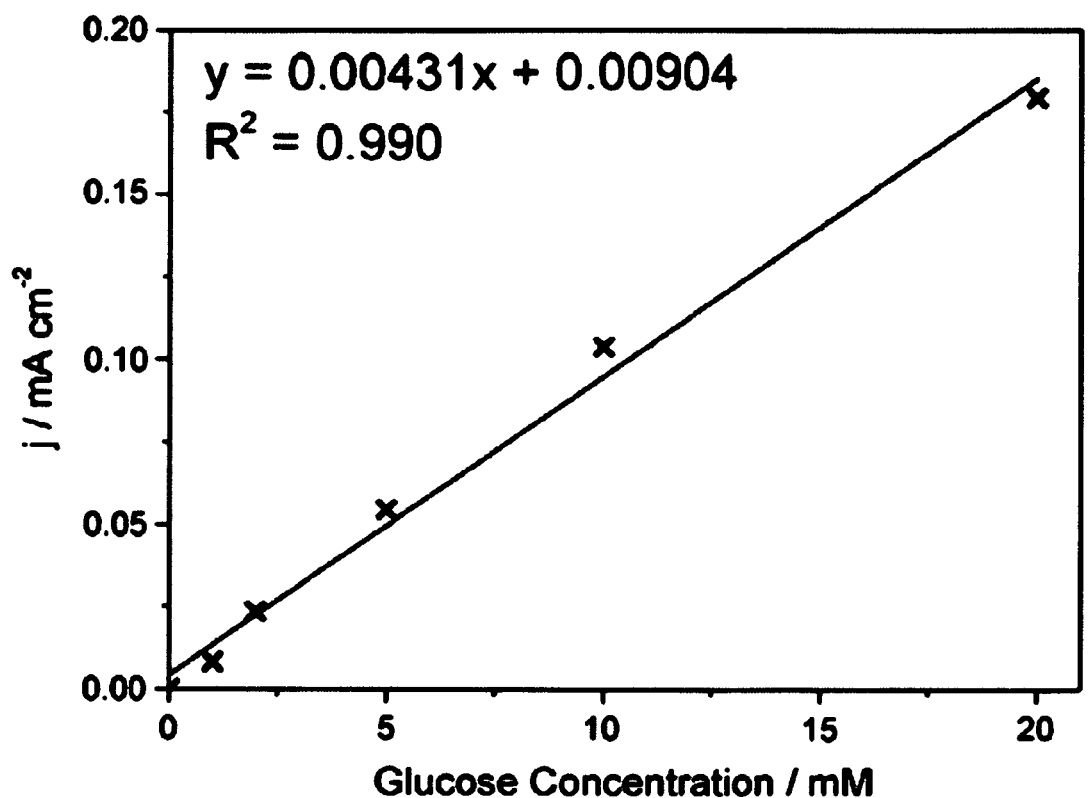

electrolyte, 1 mM, 2 mM,) 5 mM, 10 mM, and 20 mM Calibration curves of (FIG. 11) cyclic voltammetry technique and (FIG. 13) pulsed technique.

Figure 14:
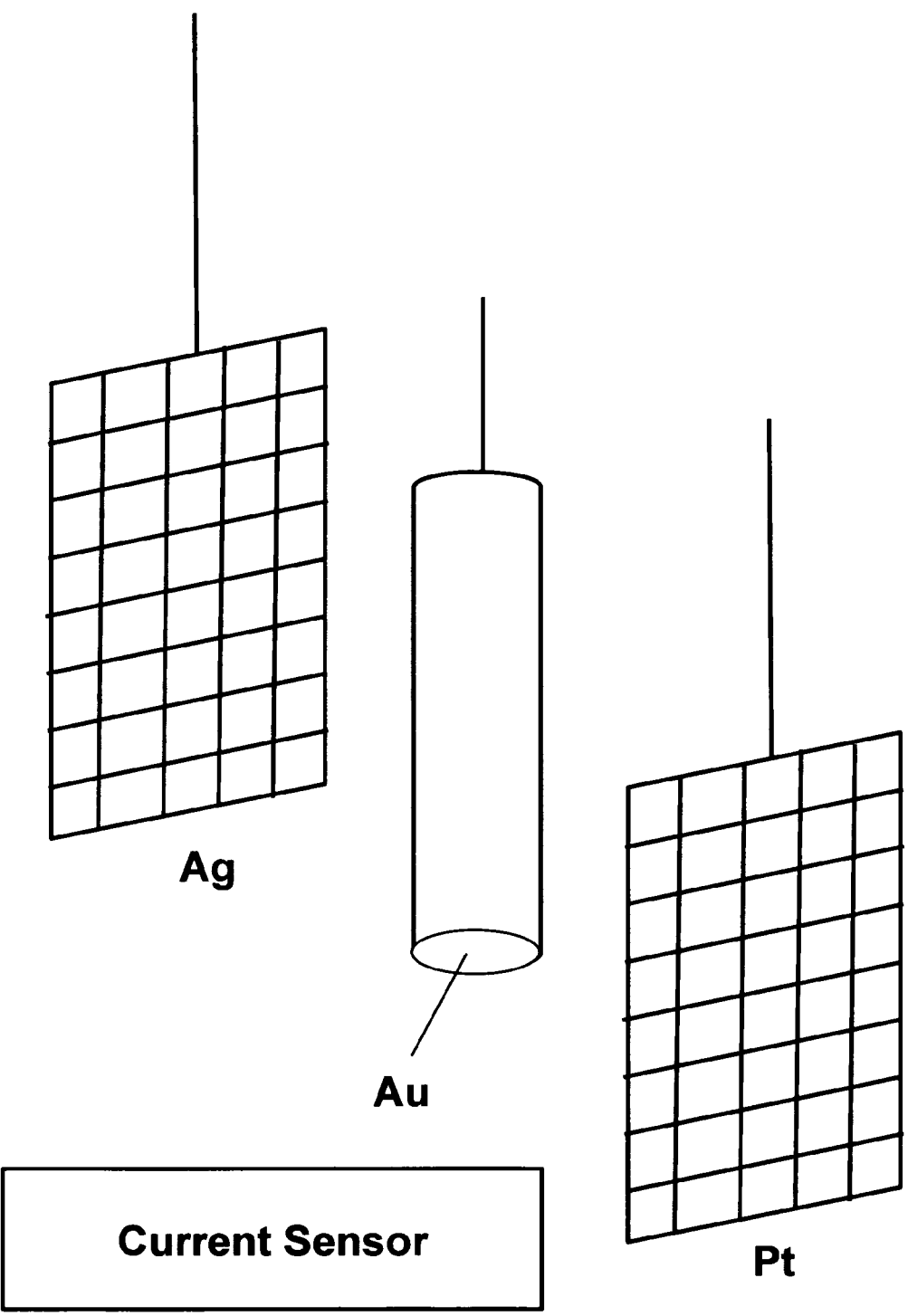

FIG. 14 shows according to exemplary embodiment of the invention a schematic of a blood glucose sensing device 1400 including an Ag electrode, an Au electrode, a Pt electrode and a sensor for sensing current.

DETAILED DESCRIPTION

Figure 1:
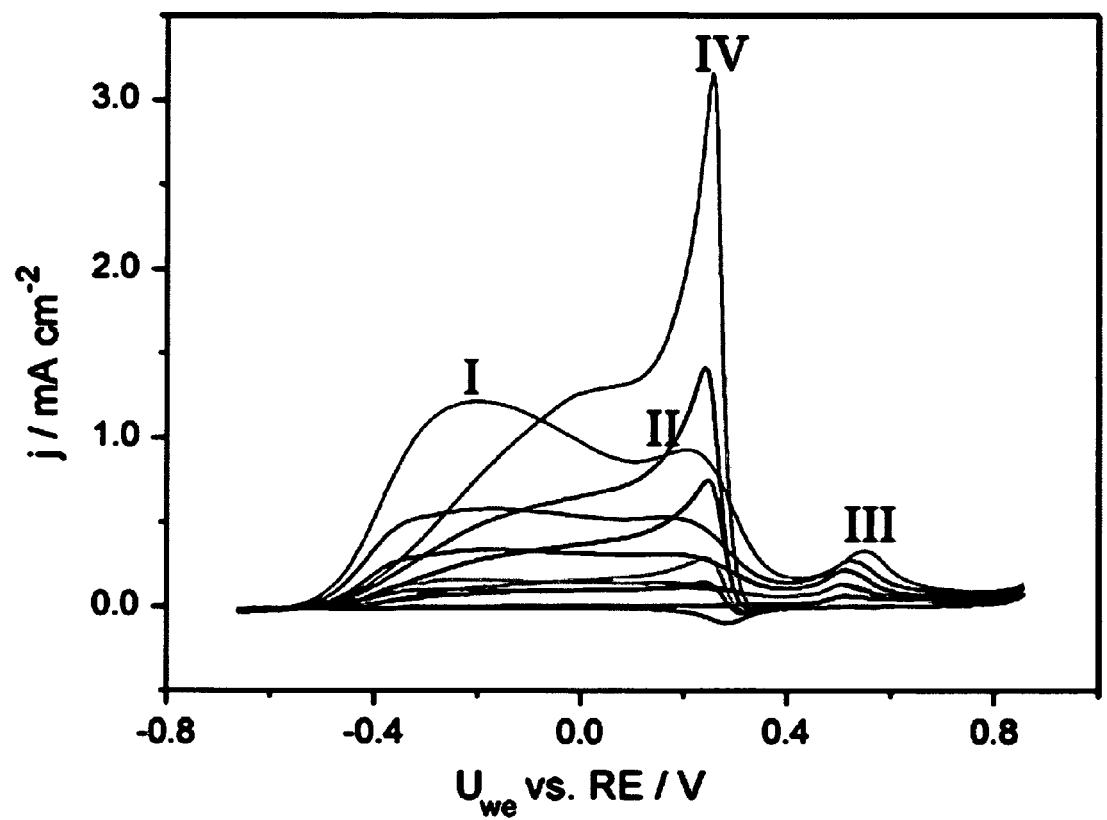
FIGS. 1-4 show according to exemplary embodiments of the invention cyclic voltammograms (20 mV s-1) (FIG. 1) and pulsed technique (chronoamperometry) of a 50 mM buffer (K2HPO4/KH2PO4) (FIG. 3), pH 11.5 solution at different glucose concentrations: electrolyte, 1 mM, 2 mM, 5 mM, 10 mM, and 20 mM, Calibration curves of (FIG. 2) cyclic voltammetry technique and (FIG. 4) pulsed technique.

To overcome at least some of the problems of chlorides in blood samples, the mechanism of glucose oxidation at gold electrodes was investigated, The glucose molecule is first electrochemically adsorbed at the surface of the electrode by dehydrogenation (peak I in FIG. 1). The dehydrogenated molecule can be transformed to gluconate either by direct oxidation or through a δ-gluconolactone intermediate step. At room temperature these two processes cannot be distinguished (peak II in FIG, 1). At higher potentials, the gold surface is oxidized to gold hydroxide (peak III in FIG. 1), which is inactive towards glucose electro-oxidation. During the cathodic scan, gold hydroxide is reduced, and therefore glucose can be readsorbed and oxidized, generating the oxidative peak in the cathodic scan (peak IV in FIG. 1).

Chloride ions inhibit the formation of the "sensing peak" in two ways:
1) In the presence of chlorides gold gets oxidised to gold tetrachloroaurate instead of forming the hydroxide (reaction III).
2) Chlorides, adsorbing at gold active sites, inhibit glucose oxidative adsorption (reaction I), first and key step of the oxidation mechanism.

In the present invention, a further solution to this problem is provided which involves a three electrodes setup, and a four-steps pulsed electrochemical detection technique (see FIG. 5).

In one example, D(+)-Glucose anhydrous, sodium chloride, potassium phosphate dibasic, potassium phosphate monobasic and silver gauze (80 mesh 0.115 mm diameter wire, 99.9% 2×2 cm) were used (e.g. from Sigma Aldrich). Gold pin electrode (Surface Area 0.0314 cm2) and platinum counter electrode were also used (e.g. from Amel Electrochemistry). The electrochemical characterization was carried out using a BioLogic VMP3 potentiostat-galvanostat multichannel equipped with EIS board, the experimental setup of the device and method has a total of four electrodes (see FIG. 5):

Two working electrodes (WE): a silver gauze for chlorides removal-pH increase (FIG. 5, steps 1 and 4) and a gold pin for glucose sensing (FIG. 5, steps 2 and 3). Their connection with the potentiostat could be switched manually. Nevertheless, in this example, they were both present in the solution during the entire experiment.

A platinum counter electrode (CE).

A double junction Ag|AgCl|KCl (3.5 M) reference electrode (RE).

Before each experiment, the gold pin electrode surface has been activated and stabilized in 0.1 M KOH by CV scans at 100 mV s-1 between −0.7 and 0.8 V vs. RE until stable voltammograms have been observed. All the measurements have been performed at room temperature under nitrogen atmosphere.

FIG. 1 shows cyclic voltammetries performed in a 50 mM buffer (K2HPO4/K3PO4), of pH 11.5 at different glucose concentrations ranging from 1 to 20 mM, corresponding to a 18-360 mg/dl glycemia range. According to our studies, these are the best operating conditions for optimal sensitivity of the return peak.

Figure 2:
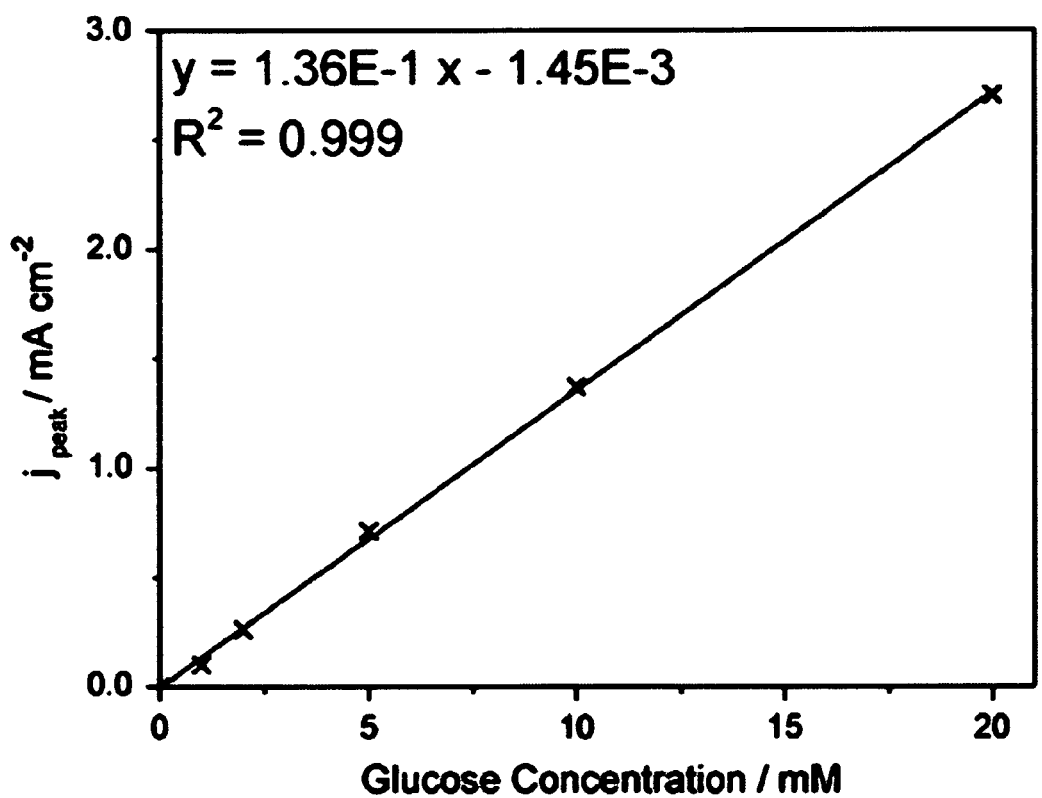
Figure 3:
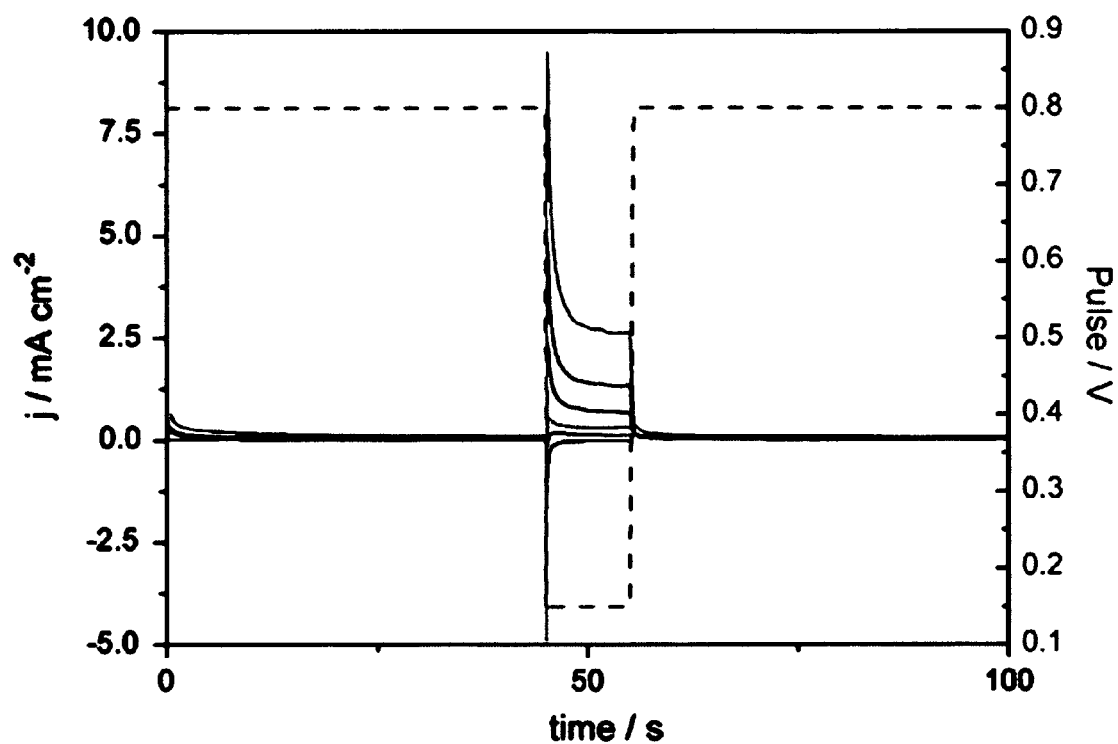
Figure 4:
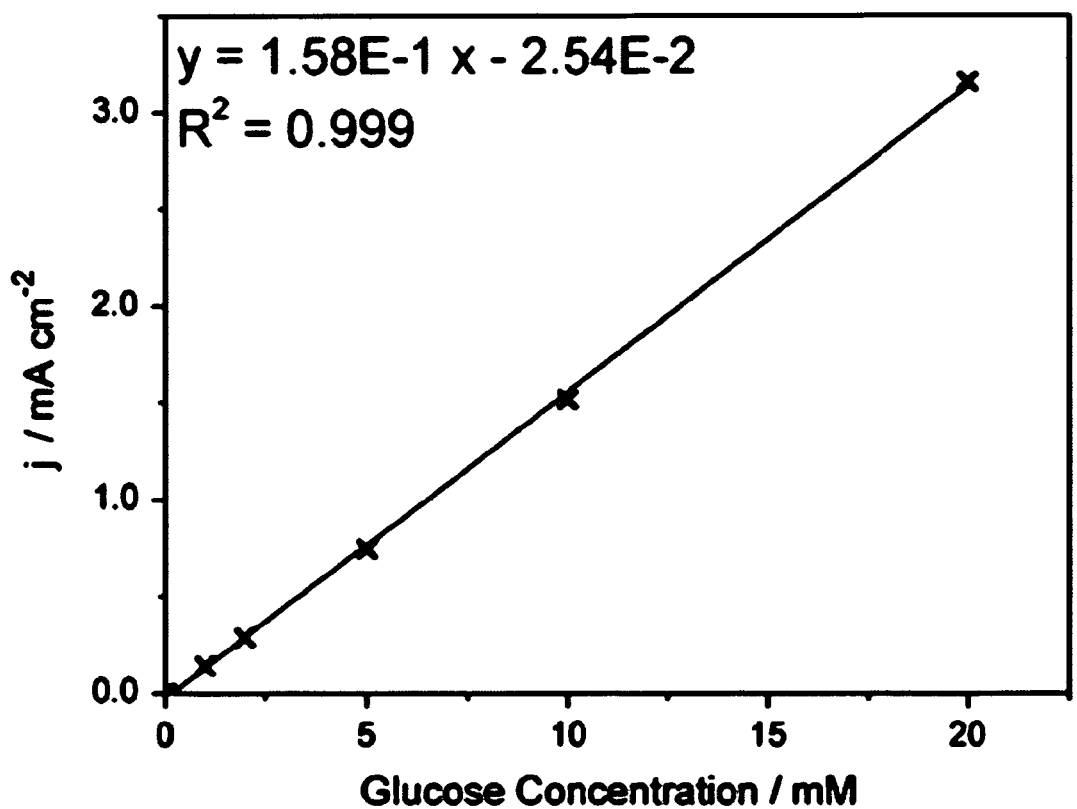

In these conditions (FIG. 2) it is evident that a linear relationship exists between the cathodic oxidative peak current density and glucose concentration in the investigated range. The preparation of the circuits to perform a CV and analyze the peak current value in a real application is complex, therefore the next step was to develop and optimize a pulsed two-step electrochemical technique, which would be easier to realize in practical applications. In the first step (0.8 V vs. RE, 40s), gold hydroxide is generated, followed by the second step (0.15V vs. RE, 15s), where gold hydroxide is reduced and glucose sensing performed. Potential and step time have been optimized for the operating conditions. In FIG. 3, it is shown that one of the 10 cycles performed for each glucose concentration to evaluate the reproducibility of the measurement. Even with this type of measurement, we saw a highly linear relationship between glucose concentration and current density as reported in FIG. 4. In this case the stationary value of current vs. glucose concentration is reported instead of the peak current value, since it is more reproducible and easier to measure in a real device application.

After proving the efficiency of the pulsed technique at pH 11.5, the next step was to test it at pH 7.4, (blood pH), while keeping all other parameters constant.

Figure 6:
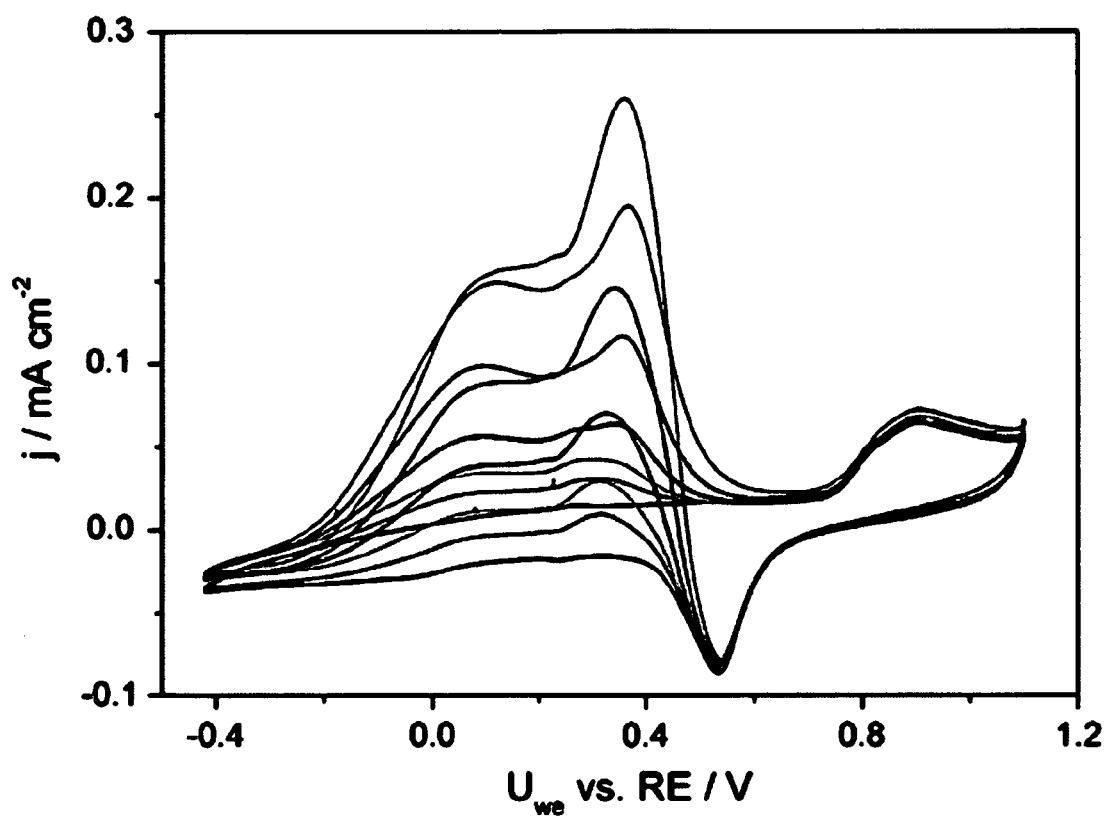
FIGS. 6-9 show according to exemplary embodiments of the invention cyclic voltammograms (20 mV s-1) (FIG. 6) and (FIG. 8) pulsed technique (chronoamperometry) of a 50 mM buffer (K2HPO4/KH2PO4), pH 7,4 (blood pH) solution at different glucose concentrations: electrolyte, 1 mM, 2 mM, 5 mM 10 mM, and 20 mM. Calibration curves of (FIG. 7) cyclic voltammetry technique and (FIG. 9) pulsed technique.
Figure 7:
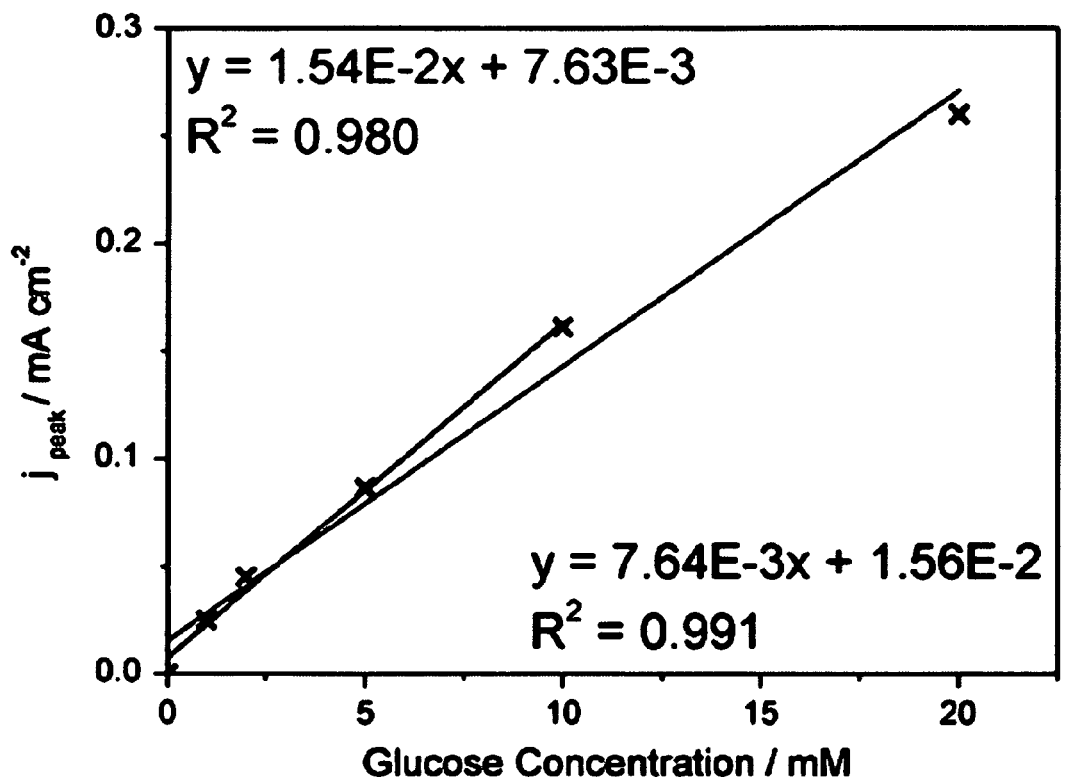

In FIG. 6 the cyclic voltammograms in the same glucose concentration range are shown. The current output is lower with respect to the previous conditions, and therefore the sensitivity on the return peak is also lower. Moreover, (FIG. 7) at higher glucose concentrations the response is not linear. This is due to the lower OH-concentration that limits the gluconate formation, as previously supra.

Figure 8:
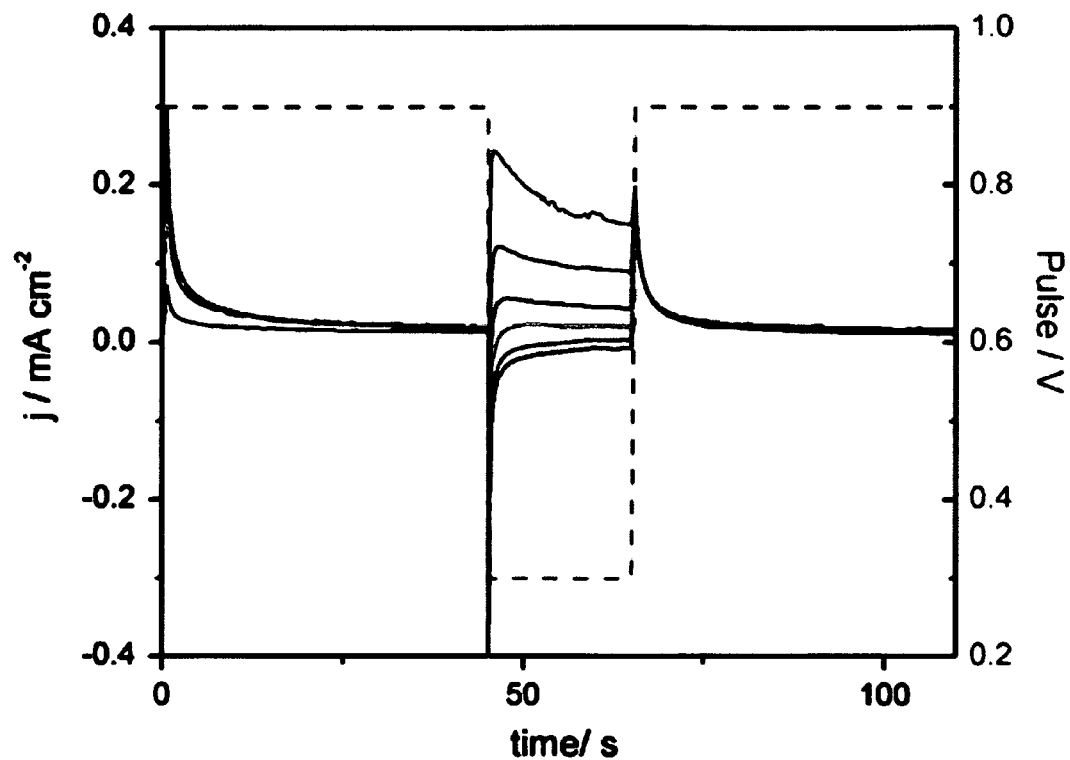
Figure 9:
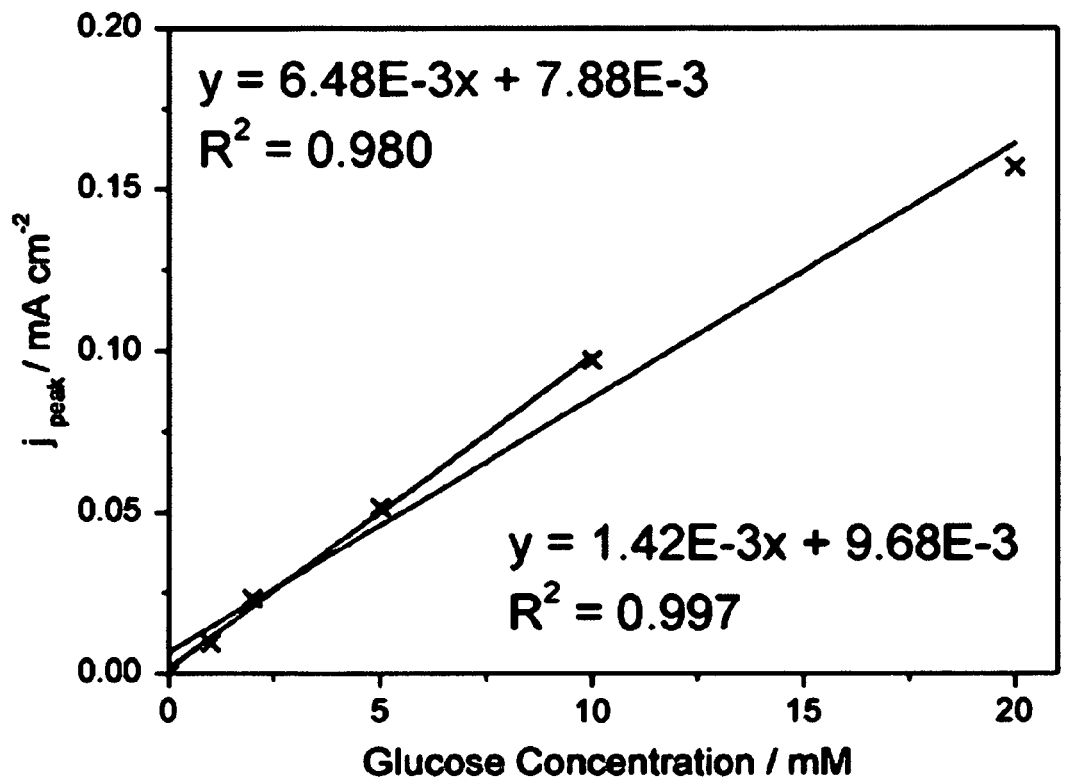

Despite this, the pulsed technique has been tested in these conditions (FIG. 8). Changing the pH requires a modification in the steps potentials, as both the gold hydroxide and return peak potentials are pH dependent. In this case, the gold hydroxide is generated at 0.9V vs. RE (40s) and the subsequent reduction/sensing step performed at 0.3 V (15 s). Thus it was demonstrated that it is possible to apply the pulsed method at blood pH, though the sensitivity and linearity range are diminished (FIG. 9).

The following step was to test the method in the presence of 100 mM potassium chloride at pH 7.4 buffered with 50 mM K2HPO4/144 KH2PO4, thus partially recreating the physiological conditions of human blood. In this case, in both CV and the pulsed technique, instead of the oxidative peak in the cathodic scan, a reduction process is observed. In the presence of chlorides, it is known that gold is oxidized to AuCl-4, a reaction that takes place at a lower potential than Au(OH)3 formation. In the cathodic scan the gold tetrachloroaurate, previously generated in the anodic scan, is reduced.

However, upon analyzing the Pourbaix diagram of gold in the presence of chlorides, it is evident that at pH values higher than 9, gold hydroxide is the most stable phase, even in the presence of up to a 2 M chloride concentration. Therefore, it is not necessary to remove all the chlorides from the solution to perform the sensing step, but it is enough to locally increase the pH to over 9. On the basis of these considerations, a four-step, three electrode (silver gauze, gold pin and platinum counter electrode) measurement has been performed. The optimized operating conditions are reported in FIG. 5.

The first step is a chronopotentionietry step, (I=10 mA) in which a silver gauze working electrode is oxidized to silver chloride, while water is reduced at the platinum counter electrode. In the overall reaction, for every chloride ion removed, a hydroxide ion is generated; therefore to shift the solution pH from 7.4 to 11.5 it is necessary to remove only 10% of the chlorides present in the solution. Thus the charge flow needs to be controlled, and it depends on the volume of solution employed (in the exemplary case we used 15 ml of solution and the charge was limited to 5 mC).

Figure 10:
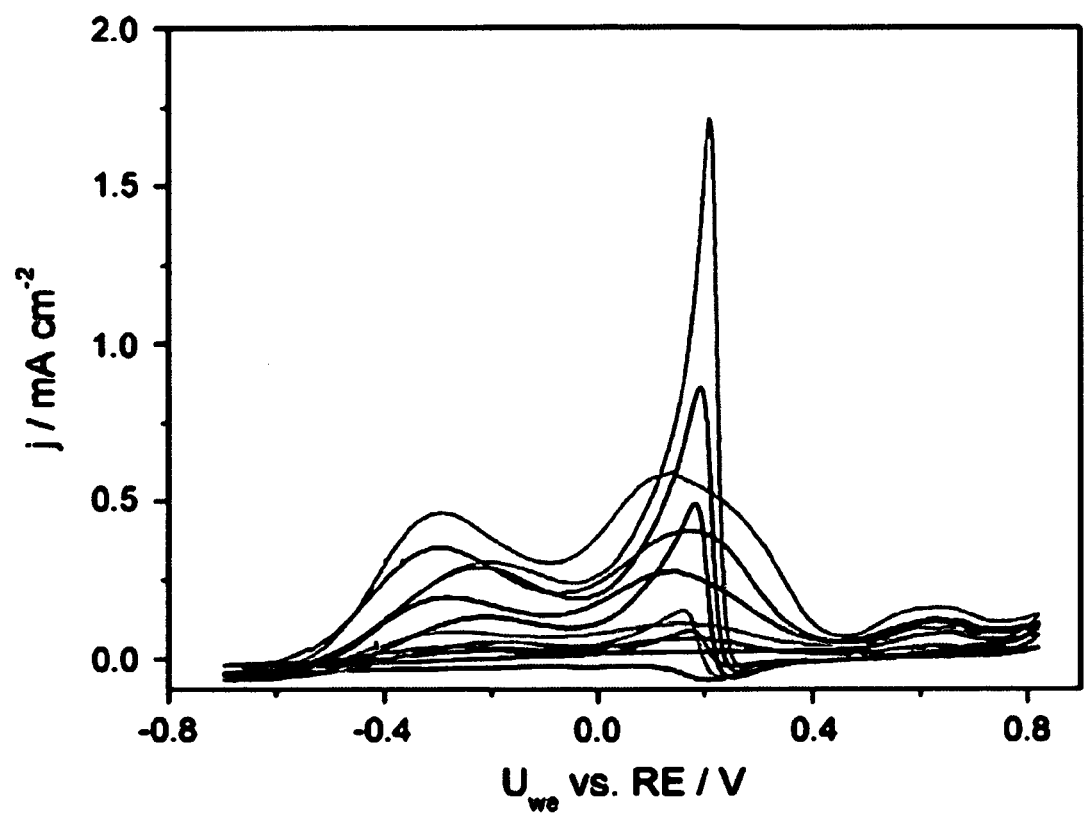
FIGs. 10-13 show according to an exemplary embodiments of the invention cyclic voltammograms (20 mV s-1) (FIG. 10) and (FIG. 12) pulsed technique (chronoamperometry) of a 50 mM buffer (K2HPO4/KH2PO4) pH 7.4, 100 mM NaCl solution at different glucose concentrations after chloride removal step.

The second step corresponds to the first step of the pulsed technique described supra, in which the gold pin electrode surface is oxidized to gold hydroxide (0.7 V vs. RE, 40 s) and subsequently reduced (0.3 V vs. RE, 15 s) in the third step: once the gold surface is regenerated, glucose can be re-adsorbed and an oxidative peak is generated. In this case, both the peaks observed in the CV, (FIG. 10) as well as the steady state current in the pulsed technique, (FIG. 11) show a very strong linear dependence on glucose concentration in the investigated range, coupled with high sensitivity. In the last (fourth) step, the silver electrode (partially covered with silver chloride from step 1) is reduced and regenerated, ready for the next sensing.

In the present invention, we identified a device and method for electrochemically sensing glucose in the presence of chlorides. These electrochemical devices and methods grant higher accuracies and sensitivities than enzymatic methods. All the materials employed (silver, platinum and gold) are fully compatible with in vivo sensing applications.

The examples reported have been tested in 15 ml of solution, which necessitates long time steps. The invention is not limited to the implementation of a miniaturized device which reduces each step time signitifantly.

What is claimed is:
1. A method of electrochemically determining glucose from a sample containing chlorides, comprising:
   (a) providing a sample containing glucose and chlorides:
   (b) removing at least part of said chlorides from said sample using a silver electrode, whereby silverchloride is formed;
   (c) establishing a first current flow between said silver electrode and a platinum current collector electrode during said removing step (b), whereby the pH of said sample increases towards basic pH;
   (d) absorbing glucose from said sample by the first forming gold hydroxide at a gold electrode and then reducing said gold hydroxide to gold at said gold electrode;

(e) establishing a second current flow between said gold electrode and said current collector platinum electrode during said gold hydroxide forming and reduction steps; and
(f) determining said glucose from said sample by analyzing oxidative current peaks caused by said absorption of said glucose.

2. The method as set forth in claim 1, wherein said basic pH is about 11.5 or larger basic pH values.

\* \* \* \* \*